US00PP19606P3

(12) United States Plant Patent
Craig et al.

(10) Patent No.: US PP19,606 P3
(45) Date of Patent: Dec. 30, 2008

(54) REGAL PELARGONIUM PLANT NAMED 'MAIDEN BERRY SWIRL'

(50) Latin Name: *Pelargonium×domesticum*
Varietal Denomination: Maiden Berry Swirl

(75) Inventors: Richard Craig, State College, PA (US); Jason Jandrew, Gilroy, CA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/713,994

(22) Filed: Mar. 5, 2007

(65) Prior Publication Data

US 2008/0222761 P1 Sep. 11, 2008

(51) Int. Cl.
*A01H 5/00* (2006.01)

(52) U.S. Cl. ..... Plt./331
(58) Field of Classification Search ..... Plt./331
See application file for complete search history.

(56) References Cited

U.S. PATENT DOCUMENTS

| | | | |
|---|---|---|---|
| PP15,770 | P2 | 5/2005 | Craig |
| PP16,934 | P2 | 8/2006 | Utecht |
| PP16,976 | P2 | 8/2006 | Utecht |
| PP17,236 | P3 | 11/2006 | Hanes |

OTHER PUBLICATIONS

UPOV International Union for the Protection of New Varieties of Plants Explanatory Notes on Variety Denominations Under the UPOV Convention 2006 [online][retrieved on Apr. 08, 2008]. Retrieved from the Internet: <http://www.upov.int/export/sites/upov/en/publications/pdf/inf_12_1.pdf>, p. 4.*

* cited by examiner

*Primary Examiner*—Annette H Para
(74) *Attorney, Agent, or Firm*—McKee, Voorhees & Sease, P.L.C.

(57) ABSTRACT

A new and distinct regal *pelargonium* cultivar is disclosed that is with compact, self-branching (without pinching) and early flowering. The flowers are light lavender with a dark pink swirl on all petals.

1 Drawing Sheet

Botanical classification: *Pelargonium×domesticum.*
Varietal denomination: cultivar 'Maiden Berry Swirl': Geraniaceae.

BACKGROUND OF THE INVENTION

This discovery relates to a new and distinct cultivar of regal *Pelargonium* (*Pelargonium×domesticum*) identified by the name of 'Maiden Berry Swirl'. The proposed commercial name is 'Maiden Berry Swirl'. The cultivar was discovered in an organized, scientifically designed breeding program conducted at University Park, Pa. 16802. The purpose of the breeding program was to create new regal *Pelargonium* genotypes with clear, bright flower colors, excellent propagation characteristics, compact growth habit, predictable and consistent flowering response and excellent post-production quality.

The new cultivar was produced from a patented cultivar ('Camelot') (pollen parent) developed at the University Park and from a selection from a commercial breeding program (SP956) (seed parent). The present invention relates to a new and distinct cultivar of regal *Pelargonium* (*Pelargonium×domesticum*) called 'Maiden Berry Swirl'. This cultivar is compact, self-branching (without pinching) and early flowering. The flowers are light lavender with a dark pink swirl on all petals.

Among the hybridizations made in 1999 was a cross-pollination of 'Camelot', a patented (PP13209) cultivar and SP956, a commercial breeding line. Seven seeds of this hybrid were sown on Sep. 9, 1999 and were identified as 99-247. Three of the seeds germinated and the seedling 'Maiden Berry Swirl' was grown to maturity and produced its first inflorescence on Feb. 20, 2000. This seedling was compact and produced many flowers with what appeared to be viable pollen. Flower color was noted as pink-rose and later modified to be lavender-rose.

The seedling was cultivated to produce a stock plant (a plant that is used to harvest asexual propagules). The selection (Maiden Berry Swirl) was first asexually propagated by cuttings at University Park, Pa. on Sep. 26, 2000. The cuttings were placed into a mist facility and produced roots. These cuttings were floral initiated under supplemental metal halide lamps, potted into a soilless medium in 15 cm containers, and grown to maturity in an acrylic-covered greenhouse utilizing standard production protocols. Floral and vegetative traits were recorded on Jan. 23, 2001.

The plants were judged to be "short in height", with "good foliage", "good branching", "good flowering" and an overall rating of "good" with an indication that the accession should be retained for future evaluation. The second asexual propagation was on Nov. 11, 2000. The plants flowered on Feb. 10, 2001. Height was noted to be "medium", foliage as "very good", and branching as "good". Flower production was excellent and overall the accession was judged "very good". A comment that was appended indicated that the selection did not abscise petals and that it was "a winner". Again we decided to retain the selection for future evaluation. Three additional trials were evaluated in 2000. All of the reproductions ran true. Subsequent evaluations were conducted in the greenhouse (four or five times annually) and garden (annually) in 2001, 2002, 2006 and 2007. The most outstanding traits of this novel cultivar are its unique flower color, its compact growth, early flowering, its floral longevity and its ability to be successfully propagated asexually.

The selection is similar to its maternal parent in ease of flowering, compact growth habit, number and quality of flowers. It appears to be similar to its paternal parent in floral longevity and reduced floral abscission. 'Maiden Berry Swirl' combines the bright salmon pink flower color of SP956 and the deep lavender floral pigmentation of 'Camelot' into a rich lavender pink. The raspberry swirl floral pattern is unlike either parent.

This cultivar, unlike many other regals, is designed to be grown in smaller containers (10–12 cm). It is self-branching and requires no pinching or growth retardants. It has excellent post-production traits. 'Maiden Berry Swirl' differs from other regal cultivars based on the unique 'raspberry swirl' in the petals.

Propagules of the selection were sent for evaluation to Connellsville, Pa. on Jul. 19, 2002 and again in the spring of 2004. The cultivar has been found to retain its characteristics through successive asexual generations.

The description of the new cultivar that is presented below was developed from plants grown in a glass greenhouse at Connellsville, Pa. Rooted cuttings were potted into 12.7 cm plastic pots containing a soilless medium and fertilized with constant fertilization at 200 ppm nitrogen and potassium. Plants were grown under 16-hr days with supplemental high-pressure sodium lamps.

BRIEF DESCRIPTION OF THE DRAWING

FIG. 1 is a photograph illustrating the new cultivar with the color being as nearly true as is possible with color illustrations of this type.

DETAILED BOTANICAL DESCRIPTION

The following detailed description set forth the characteristics of the new cultivar. Age of plant described in this data sheet is 14 weeks from a rooted cutting in a 12.7 cm plastic container in a glass greenhouse. The color measurements were recorded indoors in Connellsville, Pa. under incandescent light with additional natural light. The color standard is Pantone Process Color System.

THE PLANT

Classification:
- *Botanical.*—*Pelargonium×domesticum.*
- *Commercial.*—Regal *Pelargonium* named 'Maiden Berry Swirl'.

Time to initiate roots: About 9 days at about 21°C.
Time to develop roots: About 14 days at about 21° C.
Time to produce a finished plant from a rooted cutting: About 12 weeks in a 9 cm container.
Form: Round-mounded.
Height: 11.4 cm from medium surface to top of foliage.
Height: 17.8 cm from medium surface to top of flowers.
Plant diameter: 15.2 cm.
Plant vigor: 2 on a scale of 0–5; where 5 is extremely vigorous.
Strength: No artificial support is needed.
Branching habit: Free basal branching.
Stem:
- *Main stem length.*—10.2 cm.
- *Diameter.*—1.0 cm.
- *Color.*—S301-1.
- *Texture.*—Leathery.
- *Pubescence.*—Moderate.
- *Internode length.*—1.3 cm.

Lateral branches:
- *Length.*—Primary: 7.6–8.9 cm. Secondary: Plant not mature enough to determine.
- *Diameter.*—Primary: 0.8–1.3 cm. Secondary: Plant not mature enough to determine.
- *Internode length.*—1.0–1.3 cm.
- *Texture.*—Leathery.
- *Pubescence.*—Moderate.
- *Color.*—S301-1.

Foliage: Alternate stalked leaf attachment.
- *Stipules.*—Size: 0.4–0.9 cm. Color: S289-3.
- *Size of leaf.*—Length: 2.5–4.0 cm. Width: 2.5–5.5 cm.
- *Shape of leaf.*—Reniform.
- *Shape of apex.*—Pointed.
- *Shape of base.*—Truncated.
- *Margin.*—Serrated, lobed.
- *Texture.*—Leathery.
- *Pubescence.*—Upper surface: Light. Lower Surface: Moderate.
- *Color.*—Young leaves: Upper surface: S289-3. Lower surface: S289-4. Mature leaves: Upper surface: S293-1. Lower surface: S285-5.
- *Veins.*—Venation type: Branched, palmate.
- *Color.*—Upper surface: S293-1. Lower surface: S284-5.
- *Petioles.*—Length: 2.0–5.0 cm. Diameter: 0.2–0.3 cm. Color: S293-1.

INFLORESCENCE

Natural flowering season: Would naturally flower under cooler temperatures on west coast; requires cool temperatures and extended photoperiod to flower fully in the greenhouse after buds are initiated.
Blooming habit: Requires about 8 weeks under specific temperature and irradiance regimes to initiate floral buds.
- *Borne.*—Florets on pedicel; pedicel on peduncle.
- *Inflorescence position.*—Above foliage.
- *Inflorescence diameter.*—8–10 cm.
- *Inflorescence depth.*—5.5–6.0 cm.
- *Number of inflorescences per lateral branch.*—4–5.
- *Longevity of florets.*—About 30 days.

Florets:
- *Open florets.*—Form: Slightly cupped; petals overlap, edges ruffled. Number: 4–7 per inflorescence. Diameter: 5.5–7.0 cm. Depth: 2.5–3.0 cm.

Petals:
- *Color.*—Upper Surface: The edge of the petal is lavender S164-7. The large blotch in the center of the petal is S157-3 fading to S156-1 toward the edge of the petal. The petal is white where it is attached, and darker venation described as S167-1 branches from the center of the petal out into the center blotch. The upper two petals have a larger blotch than the bottom three petals, but the color description is the same. Lower surface: The petal is white where attached. The edges of the underside of the petal are S164-9. The upper two petals have a larger blotch in the center, S157-3, with venation of S167-1 branching into the blotch from where the petals are attached. The lower three petals have a S167-1 colored edge, but have only a slight streak of color S156-1 emanating from the petal attachment.
- *Shape.*—Teardrop.
- *Length.*—4.0–4.2 cm.

*Width.*—Lower three are 2.5 cm. Upper two are 3.5 cm.
*Apex shape.*—Rounded.
*Margin.*—Entire, ruffled.
*Number per floret.*—5.
*Texture.*—Smooth.
*Tonality from a distance.*—Light lavender with a dark pink swirl on all petals.

Petaloids: None present.

Pedicel:
*Length.*—1.5–1.7 cm.
*Diameter.*—0.2 cm.
*Color.*—S292-1.

Peduncle:
*Length.*—3.5–5.5 cm.
*Diameter.*—0.3 cm.
*Texture.*—Pubescent, leathery.
*Color.*—S293-2.

Sepals:
*Shape.*—Lanceolate.
*Width.*—0.5–0.6 cm.
*Length.*—2.0 cm.
*Color.*—S293-2.

Fragrance:
*Flower.*—None.
*Foliage.*—Fruity fragrance.

Disease resistance: None observed.

Temperature tolerance: None observed.

Drought tolerance: None observed.

REPRODUCTIVE ORGANS

Stamens:
*Number per floret.*—7.
*Filaments.*—Length: 1.8–2.0 cm. Color: White.
*Anthers.*—Shape: Elliptical. Length: 0.3 cm. Color: S167- 3.
*Pollen.*—Color: Orange when mature. Amount: Average.
*Pistils.*—Number: 1, 5–6 parted. Length: 2.0–2.2 cm.
Style. —Length: 1.4–1.5 cm. Color: S153-3.

Stigma: Shape: Twisted slightly, some curling downward or to side. Color: S170-3. Size: 0.5–0.7 cm in diameter when separated.

Ovaries: Superior and highly pubescent
*Length.*—0.4 cm.
*Width.*—0.2 cm.
*Color.*—S301-1.

Fruit: None observed.

GENERAL CHARACTERISTICS

1. Flower color is lavender with a dark pink swirl on all petals.
2. Cutting production is commercially acceptable.
3. Rooting time is about 23 days for root initiation and root development.
4. Plant habit is compact and self-branching without pinching.
5. Flowering time is dependent on the season but generally 12 weeks from a rooted cutting in a 12.7 cm container.
6. There are usually 4–5 inflorescences per branch and 4–7 florets per inflorescence.
7. Outdoor growth is average at University Park.
8. This cultivar is characterized by having very good post-production floral longevity.

I claim:

1. A new and distinct cultivar of *Pelargonium*× *domesticum* plant as shown and described.

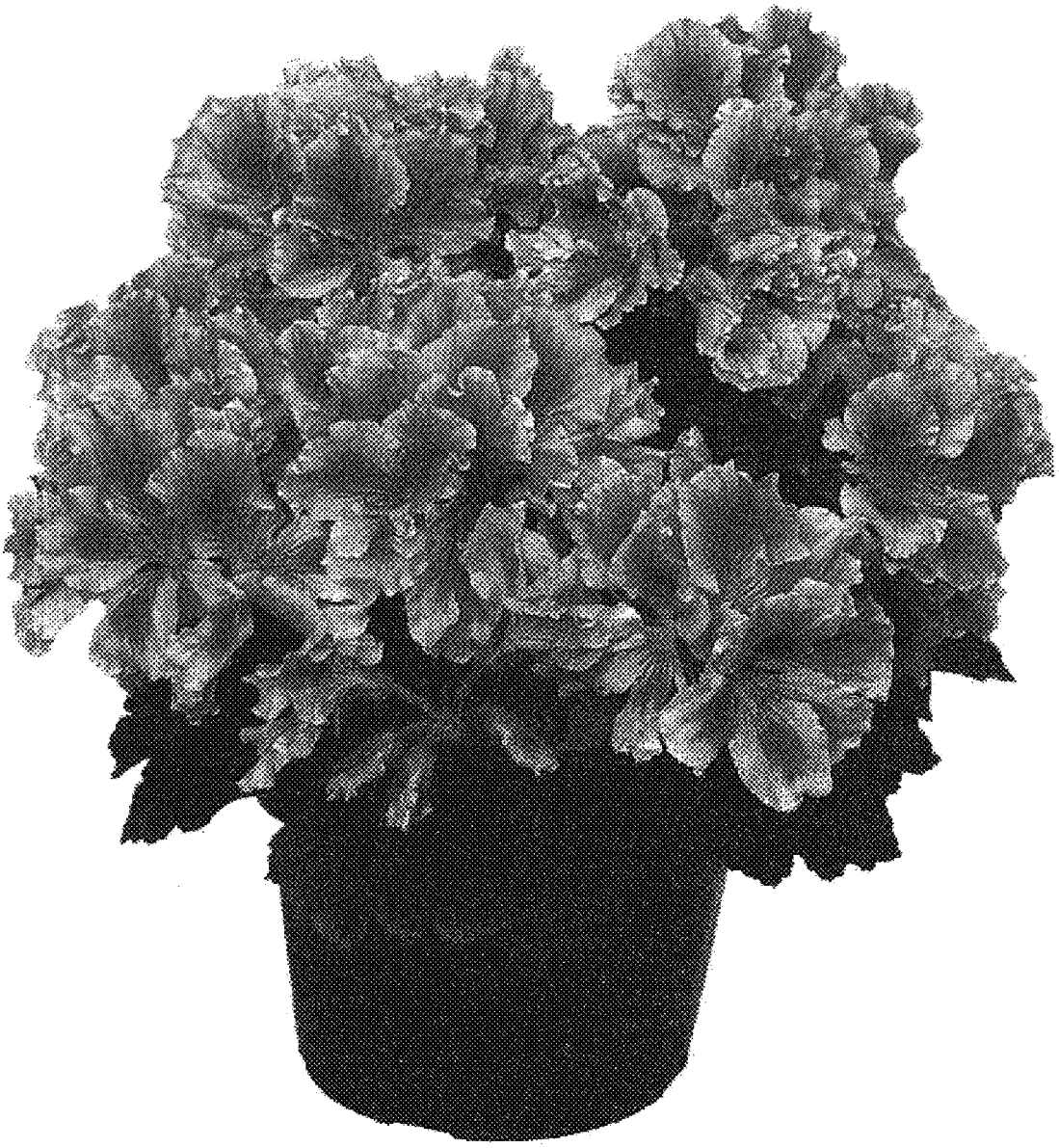

* * * * *